US008465636B2

(12) United States Patent
Sugaya et al.

(10) Patent No.: US 8,465,636 B2
(45) Date of Patent: Jun. 18, 2013

(54) AMMONIUM GAS SENSOR

(75) Inventors: Satoshi Sugaya, Kounan (JP); Shiro Kakimoto, Kasugai (JP); Hiroyuki Nishiyama, Kounan (JP); Wataru Matsutani, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 472 days.

(21) Appl. No.: 12/390,567

(22) Filed: Feb. 23, 2009

(65) Prior Publication Data

US 2009/0211906 A1 Aug. 27, 2009

(30) Foreign Application Priority Data

Feb. 22, 2008 (JP) ................................ 2008-040934
Nov. 14, 2008 (JP) ................................ 2008-291752

(51) Int. Cl.
*G01N 27/407* (2006.01)

(52) U.S. Cl.
USPC .......... 204/429; 204/424; 204/428; 73/23.31; 73/23.32

(58) Field of Classification Search
USPC ...................... 204/424–429; 73/23.31–23.32; 205/783.5–785, 781
See application file for complete search history.

(56) References Cited

U.S. PATENT DOCUMENTS 5,443,711 A * 8/1995 Kojima et al. ................ 204/429
5,518,603 A 5/1996 Furuhashi et al.
6,379,529 B1 4/2002 Wahl et al.
6,533,911 B1 3/2003 Fujita et al.
6,565,723 B1 * 5/2003 Danley et al. ................. 204/429
2001/0054553 A1 12/2001 Isomura et al.
2004/0118703 A1 * 6/2004 Wang et al. ................ 205/780.5
2006/0024202 A1 2/2006 Atsumi et al.
2007/0000780 A1 1/2007 Oya et al.
2007/0045114 A1 * 3/2007 Wang et al. ................... 204/431
2007/0246353 A1 * 10/2007 Soroushian et al. .......... 204/279
2007/0289870 A1 12/2007 Nair et al.

FOREIGN PATENT DOCUMENTS

JP 510918 A 1/1993
JP 954064 A 2/1997
JP 2001502434 A 2/2001
JP 2001108649 A 4/2001
JP 2001-174434 A 6/2001

(Continued)

OTHER PUBLICATIONS

Japanese Office Action dated Jun. 4, 2012 issued by the Japanese Patent Office in counterpart Japanese Patent Application No. 2008-291752.

*Primary Examiner* — Keith Hendricks
*Assistant Examiner* — Bach Dinh
(74) *Attorney, Agent, or Firm* — Sughrue Mion, PLLC

(57) ABSTRACT

An ammonium gas sensor is provided. The ammonium gas sensor includes: a solid electrolyte layer having oxygen ion conductivity; a detection electrode formed on one surface of the solid electrolyte layer; a reference electrode that is a counter electrode of the detection electrode; a selective reaction layer covering the detection electrode; and a protection layer covering the selective reaction layer and made from a porous material; wherein the detection electrode includes a noble metal as a main component; the selective reaction layer includes oxide represented by $A_xM_yO_z$ as a main component, where A is one or more kind(s) of metal, M is vanadium, tungsten, or molybdenum and x, y, z are atomic ratios; and the protection layer includes the oxide that is in an amount smaller than a content of the oxide included in the selective reaction layer.

9 Claims, 7 Drawing Sheets

FOREIGN PATENT DOCUMENTS

| | | | |
|---|---|---|---|
| JP | 2006058282 | A | 3/2006 |
| JP | 2007040987 | A | 2/2007 |
| WO | 2007146369 | A2 | 12/2007 |

* cited by examiner

AMMONIUM GAS SENSOR

CROSS REFERENCE TO RELATED APPLICATION

The present application claims priority from Japanese Patent Application No. 2008-040934, which was filed on Feb. 22, 2008, and from Japanese Patent Application No. 2008-291752, which was filed on Nov. 14, 2008, the disclosure of which is herein incorporated by reference in its entirety.

TECHNICAL FIELD

Apparatuses and devices consistent with the present invention relate to an ammonium gas sensor, and more particularly, to an ammonium gas sensor that is suitably used for ammonium gas concentration measurement in a combustible gas or an exhaust gas of a combustor, an internal combustion, and the like.

BACKGROUND

As a method for cleaning nitrogen oxide ($NO_x$) in an exhaust gas of an internal combustion such as a car, a urea SCR (Selective Catalytic Reduction) method has been developed. The urea SCR method is a method for reducing $NO_x$ by ammonium that is generated by adding urea to an SCR catalyst, and an ammonium gas sensor is used for measuring whether or not an ammonium concentration for reducing $NO_x$ is in an appropriate amount.

U.S. Patent Application Publication No. 2007/0045114 (FIG. 1, paragraph 0032, claim 1, hereinafter, Patent Document 1) describes a first related art gas sensor. For example, the first related art ammonium gas sensor is an electromotive force type sensor that detects an ammonium concentration based on an electromotive force between a reference electrode and a reaction electrode formed on a surface of an oxygen ion conductor. Specifically, the first related art gas sensor is a sensor in which a reaction electrode 21 and a reference electrode 22 are opposed to each other via a solid electrolyte layer 20 made from zirconium, and the reaction electrode 21 is disposed directly under a protection layer 23 that is provided on a sensor surface and made from a porous material (see Patent Document 1). In Patent Document 1, as a composition of the reaction electrode 21, oxide represented by $A_xM_yO_z$ such as $BiVO_4$ (M represents vanadium, tungsten, or molybdenum) is described.

Also, in general gas sensors, in order to prevent poisoning of a detection electrode by a component (e.g. oil component, P, Si, and the like) in a gas to be measured, a surface of the detection electrode is covered with a protection layer made from a porous material. Japanese patent unexamined patent application publication No. JP-A-2001-174434 (Hereinafter, Patent Document 2) describes a second related art gas sensor. For example, Patent Document 2 discloses a technique of adding a zirconium oxide component that is a component of a solid electrolyte serving as an underlying layer to the protection layer in order to improve a contact of the protection layer.

SUMMARY

However, the above described related art gas sensors have a few disadvantages. For example, according to the first related art ammonium gas sensor, there is the risk of stripping-off of the protection layer in a usage environment due to low contact strength between the reaction electrode and the protection layer. Therefore, the addition of oxide of the reaction electrode to the protection layer as in Patent Document 2 may be considered to be expedient, but sensitivity of the sensor can in some cases be deteriorated by use when the oxide is simply added to the protection layer. The oxide contained in the protection layer can generate a certain reaction product with a component (e.g. oil component, P, Si, or the like) in a gas to be measured (exhaust gas) to raise the risk of porous material clogging that prevents ammonium permeation to the reaction electrode or of burning of ammonium due to the generated reaction product.

Accordingly, it is an object of the present invention to provide an ammonium gas sensor capable of improving a contact between an ammonium-selective reaction layer or a selective reaction layer and a protection layer covering the ammonium-selective reaction layer or the selective reaction layer without deteriorating sensitivity of the sensor.

Illustrative aspects of the present invention address the above described disadvantages and other disadvantages not described above. However, the present invention is not required to overcome the disadvantages described above, and thus, an illustrative aspect of the present invention may not overcome any of the problems described above.

According to a first illustrative aspect of the present invention, there is provided an ammonium gas sensor comprising: a solid electrolyte layer having oxygen ion conductivity; a detection electrode formed on one surface of the solid electrolyte layer; a reference electrode that is a counter electrode of the detection electrode; a selective reaction layer covering the detection electrode; and a protection layer covering the selective reaction layer and made from a porous material; wherein the detection electrode includes a noble metal as a main component; the selective reaction layer includes oxide represented by $A_xM_yO_z$ as a main component, where A is one or more kind(s) of metal, M is vanadium, tungsten, or molybdenum and x, y, z are atomic ratios; and the protection layer includes the oxide that is in an amount smaller than a content of the oxide included in the selective reaction layer.

With such constitution, since the oxide $A_xM_yO_z$ that is the main component of the underlying layer (selective reaction layer) is contained in the protection layer, a contact between the protection layer and the selective reaction layer is improved. Further, since the content of the oxide $A_xM_yO_z$ contained in the protection layer is made smaller than that of the selective reaction layer, the protection layer is less subject to clogging, and burning of ammonium due to a generated reaction product is suppressed, thereby suppressing deterioration of sensitivity of the sensor.

Further, according to a second illustrative aspect of the present invention, there is provided an ammonium gas sensor comprising: a solid electrolyte layer having oxygen ion conductivity; a reaction electrode formed on one surface of the solid electrolyte layer; a reference electrode that is a counter electrode of the detection electrode; and a protection layer covering the reaction electrode and made from a porous material; wherein the reaction electrode includes oxide represented by $A_xM_yO_z$ as a main component, where A is one or more kind(s) of metal, M is vanadium, tungsten, or molybdenum and x, y, z are atomic ratios; and the protection layer includes the oxide that is in an amount smaller than a content of the oxide included in the reaction electrode.

With such constitution, since the oxide $A_xM_yO_z$ that is the main component of the underlying layer (reaction electrode) is contained in the protection layer, a contact between the protection layer and the reaction electrode is improved. Further, since the content of the oxide $A_xM_yO_z$ contained in the protection layer is smaller than that of the reaction electrode, the protection layer is less subject to clogging, and burning of ammonium due to a generated reaction product is suppressed, thereby suppressing deterioration of sensitivity of the sensor.

According to this invention, it is possible to obtain an ammonium gas sensor capable of improving a contact between an ammonium-selective reaction layer or a selective reaction layer and a protection layer covering the reaction electrode or the selective reaction layer without letting the protection layer to function as the reaction electrode or the selective reaction layer.

BRIEF DESCRIPTION OF THE DRAWINGS

Illustrative aspects of the present invention will be described in detail with reference to the following figures wherein.

DETAILED DESCRIPTION OF EXEMPLARY EMBODIMENTS OF THE PRESENT INVENTION

Hereinafter, exemplary embodiments of the present invention will be described.

First Exemplary Embodiment

Figure 1:
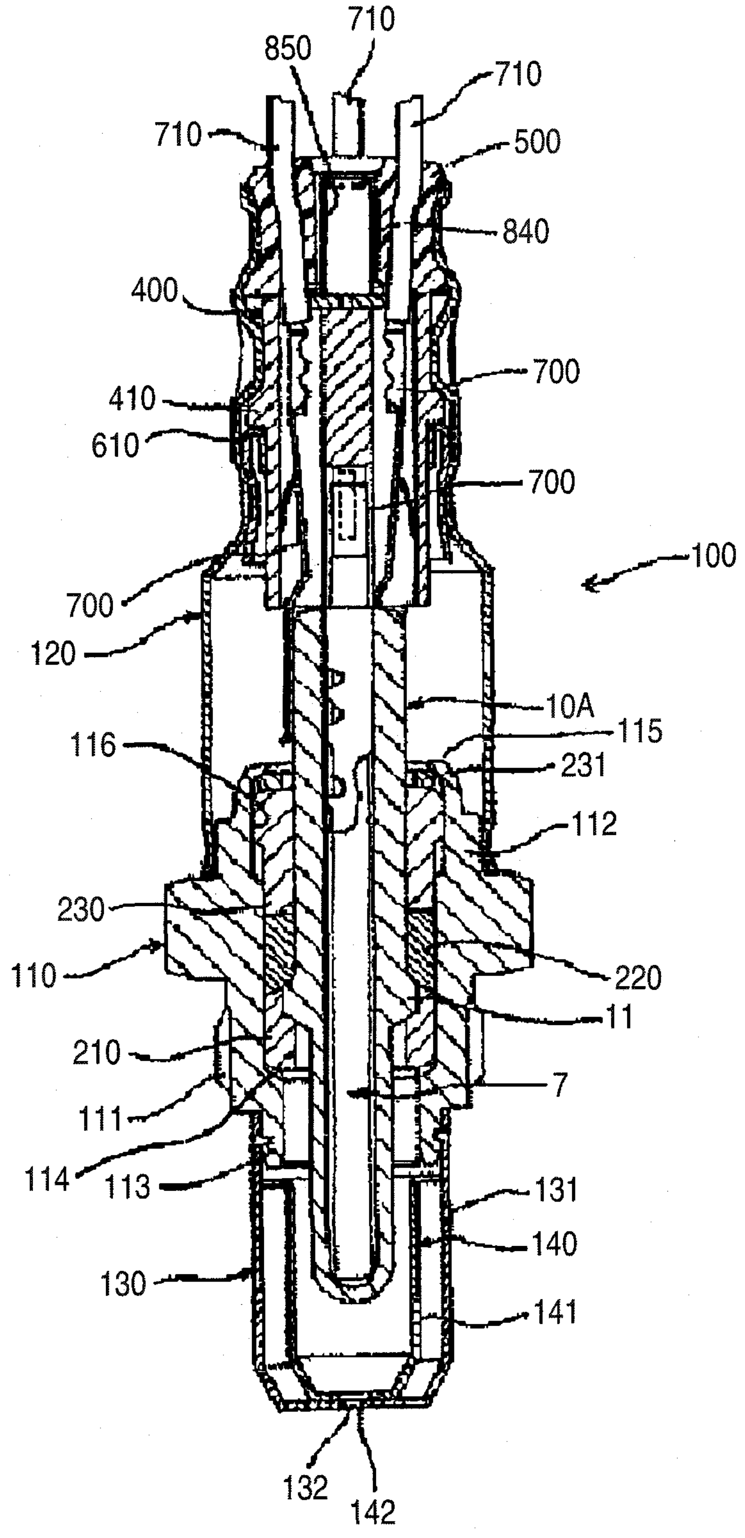
FIG. 1 is a sectional view taken along a longitudinal direction of an ammonium gas sensor according to the first exemplary embodiment of the present invention.

FIG. 1 is a sectional view taken along a longitudinal direction of an ammonium gas sensor 100 according to a first exemplary embodiment of the present invention. A front end of the ammonium gas sensor 100 is at a lower part of FIG. 1, and a rear end of the ammonium gas sensor 100 is at an upper part of FIG. 1.

The ammonium gas sensor 100 is an assembly in which a sensor element 10A detecting ammonium is assembled in a predetermined housing. The ammonium sensor 100 is provided with the sensor element 10A in the form of an elongated bottomed cylinder, a cylindrical main body fitting 110 in which a thread 111 to be used for fixation to an exhaust pipe is formed on its outer surface, a cylindrical ceramic sleeve 230 disposed so as to surround a periphery in a radial direction of the sensor element 10A, an outer cylinder 120, a cylindrical separator 400 having an insertion hole penetrating through in a direction of an axial line, and the like. A heater 7 in the form of a round bar is inserted into the cylinder of the sensor element 10A.

The main body fitting 110 has a through hole 116 penetrating through in the axis line direction, and a rack part 114 is formed as projecting in a radially inward direction of the through hole 116. The rack part 114 is formed as an inwardly tapered surface having an inclination with respect to a plane that is perpendicular to the axis line direction. The main body fitting 110 retains the sensor element 10A by the through hole 116 in a state where a front end part of the sensor element 10A is disposed at a front end outer part of the through hole 116 and a rear end part of the sensor element 10A is disposed at a rear end outer part of the through hole 116.

A ceramic holder 210 and a powder-filled layer 220 (hereinafter also referred to as a talc ring), each of which is in the form of a ring, and the ceramic sleeve 230 are laminated in this order from the front end part to the rear end part inside the through hole 116 of the main body fitting 110 so as to surround the periphery in the radial direction of the sensor element 10A. A caulking packing 231 is disposed between the ceramic sleeve 230 and a rear end part 115 of the main body fitting 110. The rear end part 115 of the main body fitting 110 is caulked via the caulking packing 231 in such a fashion as to press the ceramic sleeve 230 toward the front end side.

Further, a radially outwardly projecting flange part 11 is formed at a position between the ceramic holder 210 and the talc ring 220 in an axial direction of the sensor element 10A. Therefore, when the talc ring 220 is compressed by the above-described caulking while pressing the flange part 11, a space between the through hole 116 and the sensor element 10A is air-tightly filled so that the sensor element 10A is held.

As shown in FIG. 1, double protectors, i.e. an outer protector 130 and an inner protector 140, each being made from a metal (e.g. stainless steel) and having a plurality of introduction holes 131 and 141 are mounted on an outer periphery of a front end 113 of the main body fitting 110. A discharge outlet 132 and a discharge outlet 142 are opened on a bottom surface of the outer protector 130 and a bottom surface of the inner protector 140.

An outer cylinder 120 is fixed to an outer periphery of a rear end side 112 of the main body fitting 110. A cylindrical separator 400 contacting the rear end of the sensor element 10A and a cylindrical grommet 500 made from a fluorine rubber and contacting a rear end of the separator 400 are disposed inside the outer cylinder 120, and the separator 400 and the grommet 500 are fixed by caulking of the outer cylinder 120 in the radial direction.

A holding metal 610 having a substantially cylindrical shape is interposed between the separator 400 and the outer cylinder 120, and the flange part 410 formed at the center in the axial direction of the separator 400 is engaged with a rear end of the holding metal 610, so that the separator 400 is held by the outer cylinder 120 via the holding metal 610.

The separator 400 has four insertion holes respectively housing four connection terminals 700 (only 3 of them are shown in FIG. 1) each of which is electrically connected to a detection electrode 2A of the sensor element 10A, a reference electrode 6, and a heater 7, which are described later in this specification, and the four insertion holes are formed along a peripheral direction. A core wire of a lead wire 710 is caulked at a rear end of each of the connection terminals 700, so that the connection terminals 700 are housed in the insertion holes of the separator 400, and the lead wire 710 is housed in an insertion hole of the grommet 500 and drawn to the outside of the sensor.

A communication hole extending in the axial direction from the center of the grommet 500 is formed to allow a filter 840 and a fixing metal 850 to be inserted into the communication hole, and the filter 840 is held between the communication hole and the fixing metal 850. Since the filter 840 is formed from a fluorine resin such as PTFE (polytetrafluoroethylene) and allows the atmosphere to pass through without allowing water droplets to pass through, it is possible to introduce an ambient air (reference gas) via the communication hole to the sensor element 10A. In this exemplary embodiment, the ambient air introduced via the filter 840 is introduced to the sensor element after passing through the insertion holes (the holes in which the connection terminals 700 are disposed) provided in the separator 400.

Figure 2:
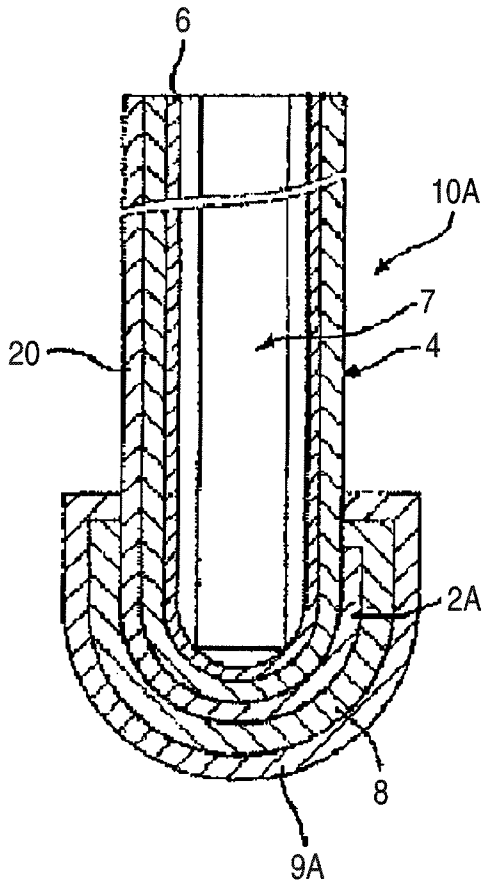
FIG. 2 is a partial sectional view showing a structure of a sensor element 10A.

Hereinafter, a structure of the sensor element 10A will be described by using a sectional view 2. FIG. 2 is a sectional view taken along a direction same as that of FIG. 1 and showing the frond end part functioning as a sensor of the sensor element 10A.

The sensor element 10A has an oxygen ion conductive solid electrolyte layer 4 having a substantially hemispherical bottom and in the form of a cylinder formed on an inner surface of the solid electrolyte layer 4, the reference electrode 6, the detection electrode 2A formed on a front end spherical part on an outer surface of the solid electrolyte layer 4, a selective reaction layer 8 covering the detection electrode 2A, a protection layer 9A covering the selective reaction layer 8 and formed from a porous material, and the heater 7 in the form of a round bar to be inserted inside the solid electrolyte layer 4.

A lead wire 20 extends from the detection electrode 2A in a longitudinal direction along an outer surface of the solid electrolyte layer 4 to be connected to the above-described connection terminal 700. The reference electrode 6 extends toward a rear end (in an upward direction in FIG. 2) of the solid electrolyte layer 4 to be connected to the connection terminal 700. The heater 7 is a heat resistant body, and a pair of lead wires is drawn from the heater 7. The lead wires are respectively connected to two of the connection terminals 700.

In order to prevent the detection electrode 2A from being exposed, the selective reaction layer 8 covers a surface and lateral end faces of the detection electrode 2A. In the same manner, in order to prevent the selective reaction layer 8 from being exposed, the protection layer 9A covers a surface and lateral end faces of the selective reaction layer 8. Therefore, the front end of the sensor element 10A is so structured that the protection layer 9A having the semispherical shape is radially outwardly projected from a main body of the sensor element 10A.

The solid electrolyte layer 4 contains a partially stabilized zirconium as a main component, for example, and exhibits oxygen ion conductivity when activated by heating with the heater 7. The reference electrode 6 is made from Pt or a Pt alloy. The detection electrode 2A is used for enhancing a very low power collection capability of the selective reaction layer 8 and made from Au or an Au alloy. The heater 7 is provided with a heating element made from W or a W alloy and Pt or a Pt alloy.

It is considered that the selective reaction layer 8 causes combustion of combustible gases (CO, HC, etc.) other than ammonium in a gas to be measured and prevents the combustible gases from reaching to the detection electrode 2A as well as from influencing on the measurement of an ammonium concentration.

The selective reaction layer 8 contains oxide represented by $A_xM_yO_z$ (A is one or more kinds of metal; M is vanadium, tungsten, or molybdenum; and x, y, and z are atomic ratios). When the selective reaction layer contains the oxide, due to a catalytic property of the selective reaction layer that is varied depending on the gases, CO and HC are burnt (react) with the oxide on the surface of the selective reaction layer, but $NH_3$ passes through the selective reaction layer without being burnt and reacts at an interface between the electrode and the solid electrolyte, thereby enabling detection of ammonium only.

Examples of A include one or more kinds selected from the group consisting of bismuth, lanthanum, strontium, calcium, copper, gadolinium, neodymium, yttrium, samarium, and magnesium.

Specific examples of $A_xM_yO_z$ include $V_2O_5$, $Cu_2(VO_3)_2$, $WO_3$, $MoO_3$, and $BiVO_4$. For example, the selective reaction layer 8 containing $BiVO_4$ is obtainable by mixing a vanadium oxide ($V_2O_5$) powder and a bismuth oxide ($Bi_2O_3$) powder at 1:1 (molar ratio) into a paste, followed by calcination and the like.

The selective reaction layer 8 contains $A_xM_yO_z$ as a main component, and a content of $A_xM_yO_z$ is larger the better. The selective reaction layer may be formed only of $A_xM_yO_z$. In this invention, the term "main component" means that a content of the component is 50 mol % or more. It is necessary that the selective reaction layer is a porous body since the selective reaction layer is required to allow the $NH_3$ gas to pass therethrough, but the porous body is obtained by calcinating the $A_xM_yO_z$ oxide in this exemplary embodiment.

The protection layer 9A prevents the underlying layer (selective reaction layer 8) from being poisoned and is formed of a porous material containing at least one kind selected from the group consisting of $Al_2O_3$, $MgAl_2O_4$, $SiO_2$, $SiO_2/Al_2O_3$, zeolite, and SiC. Since the protection layer 9A contains the above-described oxide represented by $A_xM_yO_z$, it is possible to improve a contact between the protection layer 9A and the selective reaction layer 8. A composition of $A_xM_yO_z$ contained in the protection layer 9A may not always be the same as $A_xM_yO_z$ contained in the selective reaction layer 8, but the identical composition further improves the contact.

It is possible to form the protection layer 9A by mixing the above-described porous material and $A_xM_yO_z$, followed by spraying on the surface of the selective reaction layer 8, but this formation method is not limitative When $A_xM_yO_z$ is contained in the protection layer 9A, sensitivity of the sensor can be deteriorated by use. It is considered that $A_xM_yO_z$ can generate a certain reaction product with a component (e.g. oil component, P, Si, or the like) in a gas (exhaust gas) to be measured to cause clogging of the porous material, thereby preventing ammonium from permeating to the underlying layer or thereby causing burning of ammonium due to the generated reaction product. Therefore, it is necessary that the content of $A_xM_yO_z$ in the protection layer 9A is smaller than the oxide contained in the selective reaction layer 8, and it is preferable that a component selected from the above-described group consisting of $Al_2O_3$, $MgAl_2O_4$, $SiO_2$, $SiL_2/Al_2O_3$, zeolite, and SiC is a main component of the protection layer 9A. When the content of $A_xM_yO_z$ in the protection layer 9A is larger than the oxide (of $A_xM_yO_z$) contained in the selective reaction layer 8, the sensitivity of the sensor is deteriorated. Also, an $A_xM_yO_z$ content in the protection layer 9A in the vicinity of an interface between the protection layer 9A and the selective reaction layer 8 may preferably be 10 mol % or less. When the $A_xM_yO_z$ content in the protection layer 9A exceeds 10 mol %, the sensitivity of the sensor tends to be deteriorated by use.

A lower limit of the $A_xM_yO_z$ content in the protection layer 9A in the vicinity of the interface between the protection layer 9A and the selective reaction layer 8 may preferably be 0.1 mol % or more, and it is possible to ensure the contact between the selective reaction layer 8 and the protection layer 9A by positively adding the oxide to the protection layer 9A. When the content is less than 0.1 mol %, since the oxide is not added positively to the protection layer 9A, the contact between the selective reaction layer 8 and the protection layer 9A can be deteriorated in some cases. Further, it is possible to ensure sufficient sensor sensitivity at an initial state of the ammonium gas sensor 100 when the content is 1 mol % or more.

The content of $A_xM_yO_z$ in the protection layer 9A may ordinarily be such that the content in the vicinity of the interface with the selective reaction layer 8 and a content in the vicinity of a surface of the protection layer are substantially identical with each other, and the content in the vicinity of the surface of the protection layer 9A may preferably be smaller. With such constitution, it is possible to maintain the sufficient contact between the selective reaction layer 8 and the protection layer 9A as well as to prevent the sensor sensitivity from being deteriorated. The above-described difference in content of $A_xM_yO_z$ may be realized by diffusing $A_xM_yO_z$, in the selective reaction layer 8 to the vicinity of the interface of the protection layer 9A by calcination during production of the sensor element 10A.

It is possible to detect the content of $A_xM_yO_z$ in the protection layer 9A in the vicinity of the interface between the protection layer 9A and the selective reaction layer 8 by obtaining a sectional structure of the protection layer 9A; identifying a crystal structure of the oxide containing the component A or the component M using XRD (X-ray diffraction) and XPS (X-ray Photoelectron Spectroscopic Analysis); and detecting a concentration of $A_xM_yO_z$ (calculated by conversion from the component A and the component M) contained in a region of 1 $\mu m^2$ (1 μm×1 μm) from the interface between the protection layer 9A and the selective reaction layer 8 to the protection layer 9A by EPMA (X-ray micro-analyzer). Also, in the case where the identification of oxide from the sectional structure of the protection layer 9A is difficult due to the observation region, it is possible to define an amount of an existing metal component that belongs to the oxide component of the selective reaction layer 8 and exists in the protection layer 9A by collecting the protection layer 9A in the vicinity of the interface between the protection layer 9A and the selective reaction layer 8 and employing the identification of the oxide or chemical analysis (ICP).

It is possible to detect the content of $A_xM_yO_z$ in the protection layer 9A in the vicinity of the surface of the protection layer 9A by obtaining a sectional structure of the protection layer 9A and detecting a concentration of $A_xM_yO_z$ (calculated by conversion from the component A and the component M) contained in a region of 1 $\mu m^2$ (1 μm×1 μm) from the surface of the protection layer 9A to the inside of the protection layer 9A using EPMA (X-ray Micro-Analyzer).

Further, a thickness of a part of the protection layer having the oxide content of 0.1 to 10 mol % is equal to or less than a thickness of the selective reaction layer or the reaction electrode. With such constitution, it is possible to sufficiently maintain the contact between the protection layer and the selective reaction layer, and it is possible to further prevent the deterioration in sensitivity of the sensor due to the use that is otherwise caused by generation of a certain reaction product between the oxide $A_xM_yO_z$ and a component in the gas to be measured.

The selective reaction layer or the reaction electrode may contain at least one of $A_xO_z$ and $M_yO_z$ (A is one or more kind(s) of metal; M is vanadium, tungsten, or molybdenum; and x, y, and z are atomic ratios), thereby further enhancing the ammonium selectivity. Specific examples of $A_xO_z$ and $M_yO_z$ include $Bi_2O_3$, $V_2O_5$, and the like.

Hereinafter, one example of an operation of the ammonium gas sensor 100 will be described. After activating the solid electrolyte layer 4 by heating with the heater 7, the solid electrolyte layer 4 is exposed to a gas to be measured, so that the gas to be measured permeates into the selective reaction layer 8 from the protection layer 9A, and combustible gases (CO, HC, and the like) are burnt in the selective reaction layer 8, thereby enabling an ammonium gas from which the combustible gases are eliminated to reach the detection electrode 2A.

The detection electrode 2A is opposed to the reference electrode 6 via the solid electrolyte layer 4, and the reference electrode 6 is exposed to an ambient air (reference atmosphere) via a filter of the grommet 500 (FIG. 1). Therefore, a sensor output is obtained from an electromotive force (potential difference) occurred between the detection electrode 2A and the reference electrode 6 in accordance with an ammonium concentration in the gas to be measured, thereby making it possible to detect the ammonium concentration.

Hereinafter, one example of a production method of the sensor element 10A in the ammonium gas sensor 100 will be described. A powder of a material (partially stabilized zirconium containing 4.5 mol % of $Y_2O_3$, for example) for a solid electrolyte layer is filled, and the powder is pressure-molded in to a bottomed cylinder, followed by calcination (at 1490° C., for example), thereby obtaining the solid electrolyte layer 4.

Subsequently, non-electrolytic Pt plating is performed on an inner surface of the solid electrolyte layer 4 to form a Pt layer to be used as a reference electrode 6. Meanwhile, after dispersion-mixing an Au powder, a zirconium powder, an organic solvent, and a dispersant, predetermined amounts of a binder and a viscosity adjuster are added, and wet mixing is performed to obtain a paste. This paste is printed and dried on a part to be used as a detection electrode 2A and a lead wire on an outer surface of the solid electrolyte layer 4, and the whole part is calcinated (at 1000° C. for 1 hour, for example) to form the detection electrode 2A and the lead wire.

After dispersion-mixing a vanadium oxide ($V_2O_5$) powder and a bismuth oxide ($Bi_2O_3$) powder prepared in a molar ratio of 1:1, an organic solvent, and a dispersant, predetermined amounts of a binder and a viscosity adjuster are added, and a wet mixing is performed to prepare a paste. This paste is printed and dried in such a fashion as to cover the detection electrode 2A to obtain a selective reaction layer precursor.

Subsequently, after dispersion-mixing a vanadium oxide ($V_2O_5$) powder and a bismuth oxide ($Bi_2O_3$) powder prepared in a molar ratio of 1:1, a spinel ($MgAl_2O_4$) powder, an organic solvent, and a dispersant, predetermined amounts of a binder and a viscosity adjuster are added, and a wet mixing is performed to prepare a paste. This paste is printed and dried in such a fashion as to cover the selective reaction layer precursor to obtain a protection layer precursor.

The whole body is calcinated (at 750° C. for 10 minutes, for example) to obtain a selective reaction layer 8 and a protection layer 9A to obtain the sensor element 10A. The thus-obtained sensor element 10A is assembled as the ammonium gas sensor 100 as described above.

In the case of forming the layer containing $A_xM_yO_z$ (the selective reaction layer and the protection layer in the first exemplary embodiment) by printing and calcinating the paste, a calcination temperature may preferably be adjusted between 650° C. to 1000° C.

Second Exemplary Embodiment

Hereinafter, an ammonium gas sensor according to a second exemplary embodiment of the present invention will be described. The ammonium gas sensor according to the second exemplary embodiment is the same as that of the ammonium gas sensor according to the first exemplary embodiment except for a structure of a sensor element 10B.

Figure 3:
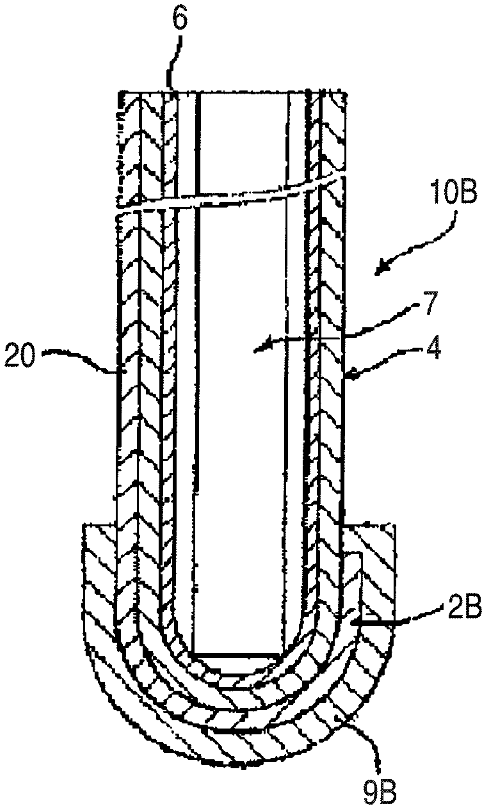
FIG. 3 is a partial sectional view showing a structure of a sensor element 10B.

FIG. 3 is a sectional view showing the structure of the sensor element 10B, and the constituent parts same as those of the sensor element 10A of the first exemplary embodiment will be denoted by the same reference numerals to omit the description.

The sensor element 10B is different from the sensor element 10A in the features that: a reaction electrode 2B is used in place of the detection electrode 2A and the selective reaction layer 8 of the first exemplary embodiment; and a surface of the reaction electrode 2B is directly covered with a protection layer 9B. In the second exemplary embodiment, the reaction electrode 2B itself has the oxide represented by $A_xM_yO_z$ as a main component. Therefore, the combustible gases are burned on the surface of the reaction electrode 2B, and ammonium from which the combustible gases are eliminated reaches to the surface of the solid electrolyte body 4 to cause an electromotive force between the solid electrolyte body 4 and the reference electrode 6, thereby enabling detection of an ammonium concentration. That is, the reaction electrode 2B has a very low power collection capability in addition to the ammonium selectivity (causing combustible gases such as CO and HC to burn), and the sensor output is obtained by using the very low power collection capability.

In the case of the sensor element 10B, since the burning of the combustible gases and the ammonium decomposition are performed on one electrode (reaction electrode 2B), sensitivity of the sensor tends to be slightly lowered as compared to the first exemplary embodiment that is provided with the selective reaction layer 8.

In the second exemplary embodiment, also, since the protection layer 9B contains the above-described oxide represented by $A_xM_yO_z$, it is possible to improve a contact between the protection layer 9B and the reaction electrode 2B. Since a content of $A_xM_yO_z$ in the protection layer 9B is smaller than the content of the oxide ($A_xM_yO_z$) in the reaction electrode 2B, it is possible to suppress deterioration of the sensitivity of the sensor.

Third Exemplary Embodiment

Hereinafter, an ammonium gas sensor according to a third exemplary embodiment of the present invention will be described. The ammonium gas sensor according to the third exemplary embodiment is the same as that of the ammonium gas sensor according to the first exemplary embodiment except for that a sensor element 10C has a plate-like shape. In the third exemplary embodiment, the constituent parts same as those of the sensor element 10A of the first exemplary embodiment will be denoted by the same reference numerals to omit the description.

Figure 4:
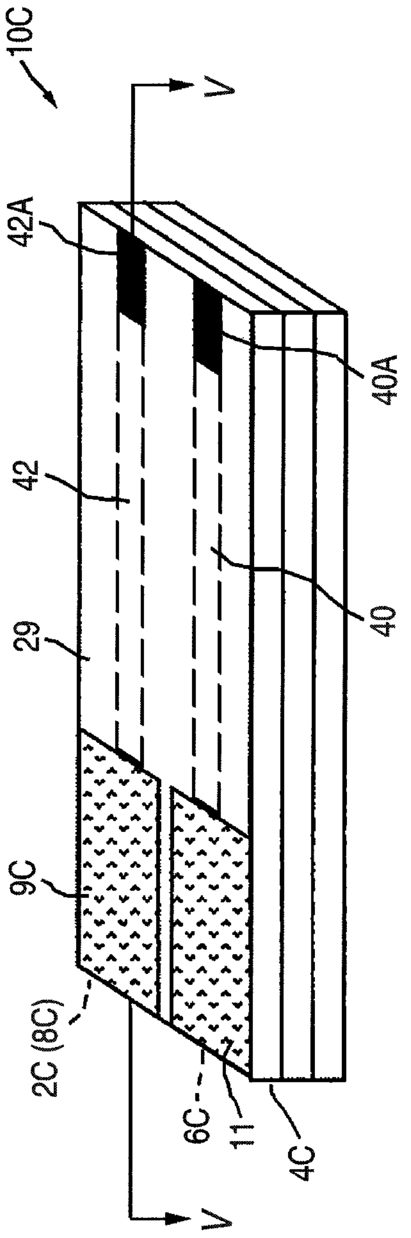
FIG. 4 is a partial sectional view showing a structure of a sensor element 10C.
Figure 6:
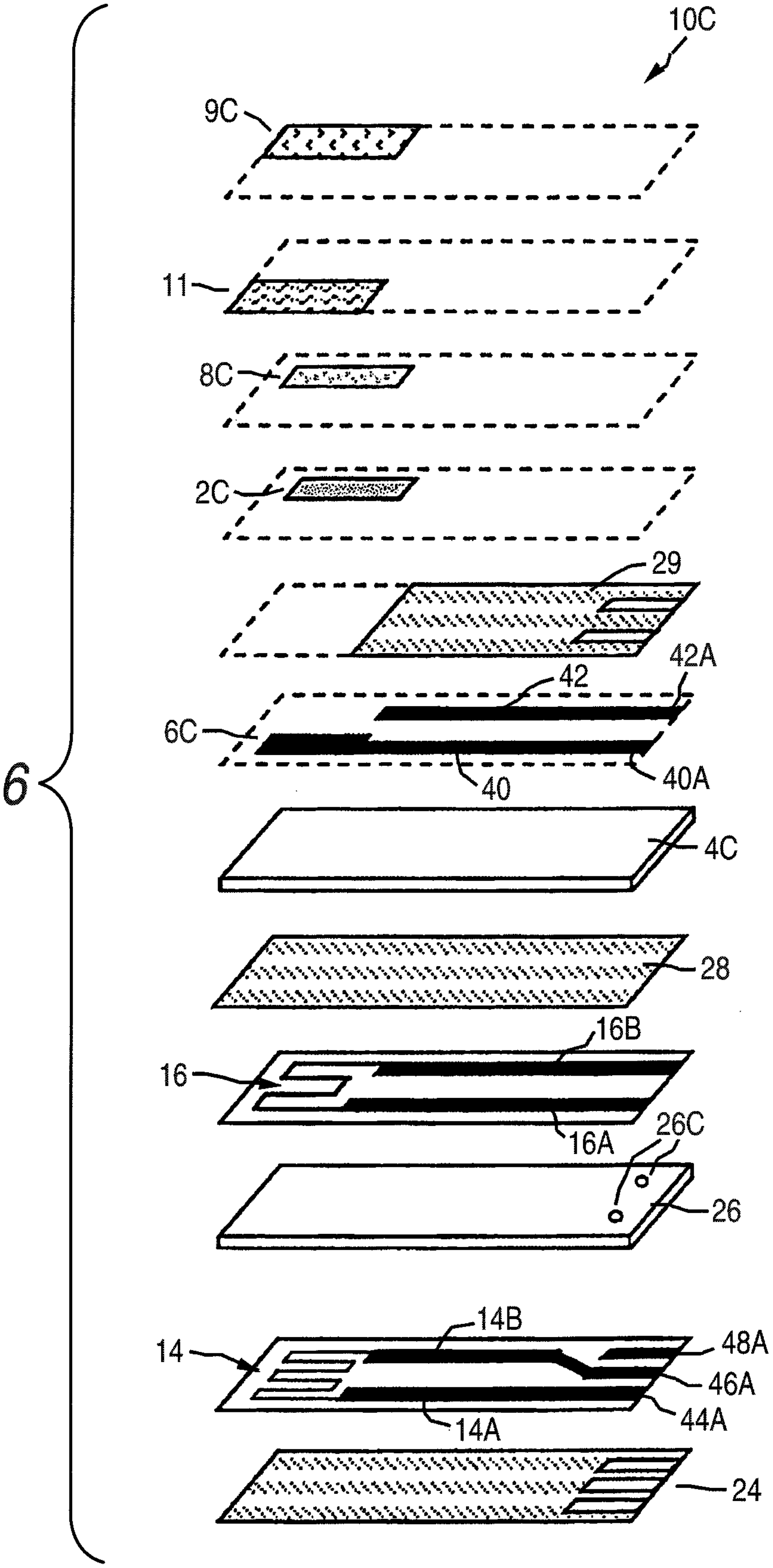
FIG. 6 is a breakdown diagram of a sensor element 10C.

As shown in FIG. 4, the sensor element 10C is in the form of a long plate, and a detection electrode 2C and a reference electrode 6C are disposed (see FIG. 6) at a front end part (left part) on one surface (upper surface of FIG. 4) of a plate-like solid electrolyte layer 4C, and the detection electrode 2C and the reference electrode 6C are separated from each other in a direction perpendicular to a longitudinal direction of the sensor element 10C. A selective reaction layer 8C (see FIG. 6) covers a surface of the detection electrode 2C, and a protection layer 9C covers a surface of the selective reaction layer 8C. The solid electrolyte layer 4C, the detection electrode 2C, the reference electrode 6C, the selective reaction layer 8C, and the protection layer 9C may have compositions same as those of the corresponding parts of the first exemplary embodiment, i.e. of the solid electrolyte layer 4, the detection electrode 2, the reference electrode 6, the selective reaction layer 8, and the protection layer 9.

A second protection layer 11 covers the reference electrode 6C, and the second protection layer 11 and the protection layer 9C are separated from each other in the direction perpendicular to the longitudinal direction of the sensor element 10C. A composition of the second protection layer 11 is not particularly limited and may be the same as that of the protection layer 9C, but it is preferable that the second protection layer 11 does not contain the oxide contained in the selective reaction layer 8C. With such constitution, it is possible to prevent deterioration of sensor sensitivity as well as to protect the reference electrode.

Lead wires 40 and 42 (see FIG. 6) to which the detection electrode 2C and the reference electrode 6C are connected extend from a rear end of an upper surface of the sensor element 10C, and rear ends of the lead wires 40 and 42 form electrode terminals 40A and 42A. An insulation layer 29 is formed in such a fashion as to cover the lead wires 40 and 42. The electrode terminals 40A and 42A are not covered with the insulation layer 29. A heater and electrode terminals 44A, 46A, and 48A (see FIG. 6) are exposed at a rear end of a lower surface of the sensor element 10C.

Figure 5:
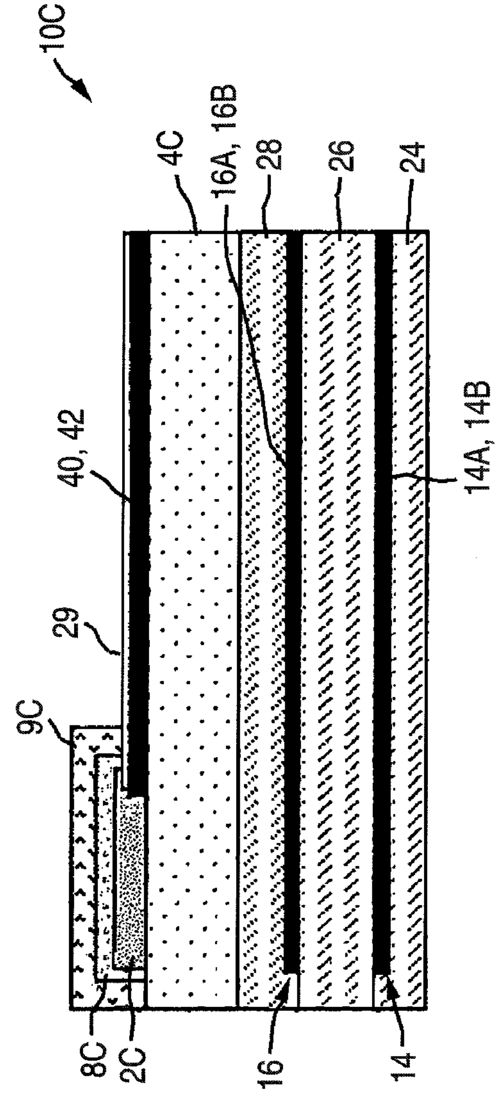
FIG. 5 is a sectional view taken along the line V-V of FIG. 4.

FIG. 5 is a sectional view taken along the line V-V of FIG. 4.

The sensor element 10C has a structure wherein insulation layers 24, 26, and 28 made from alumina are laminated, and the solid electrolyte layer 4C is laminated on an upper surface of the insulation layer 28.

A temperature sensor 14 which is a resistance temperature detector is disposed between the insulation layers 24 and 26, and a heater 16 which is a heating resistance for heating the sensor element 10C is disposed between the insulation layers 26 and 28. Also, lead wires 14A and 14B extend from the temperature sensor 14 along the longitudinal direction. Also, lead wires 16A and 16B extend from the heater 16 along the longitudinal direction to be connected to the electrode terminals 44A, 46A, and 48A provided on the lower surface of the insulation layer 24 via a through hole (not shown) formed on the insulation layer 26. An applied voltage of the heater 16 is controlled based on a measurement value of the temperature sensor 14, so that the solid electrolyte layer of the sensor element 10C is heated and controlled to an optimum temperature (activation temperature).

Each of the temperature sensor 14, the heater 16, and the lead wires 14A, 14B, 16A, and 16B contains platinum as a main component.

As each of the insulation layers 24, 26, and 28, a ceramic sintered body having an insulation property may be used, and examples thereof include a ceramic of alumina, mullite, or the like.

Hereinafter, one example of a production method of the sensor element 10C will be described briefly with reference to a breakdown diagram 6. After dispersion-mixing an Au powder, an organic solvent, and a dispersant in a trommel, predetermined amounts of a binder and a viscosity adjuster are added, and wet mixing is performed to obtain a slurry. A sheet is molded from the slurry by a doctor blade method, followed by annealing to prepare an alumina insulation layer 26 of a relatively thick (300 μm, for example) green sheet that is to be used as a main body of the sensor element. An electrode paste (hereinafter referred to as "Pt-based paste") containing Pt, alumina (inorganic oxide to be used as a shared green body), a binder, and an organic solvent is subjected to screen printing to form the heater 16 (and lead wires 16A and 16B extending from the heater).

The through hole 26C is opened at a rear end of the insulation layer 26.

Screen printing of the Pt-based paste is performed on a lower surface of the insulation layer 26 to form the temperature sensor 14 (and lead wires 14A and 14B extending from the temperature sensor and the electrode terminals 44A, 46A, and 48A), and screen printing of a paste containing alumina, a binder, and an organic solvent is performed on a surface of the temperature sensor 14 to form the insulation layer 24. The electrode terminals 44A, 46A, and 48A are exposed without being covered. The electrode terminal 44A is connected to the lead wire 14A as well as to the lead wire 16A via the through hole 26C. The electrode terminal 46A is connected to the lead wire 14B. The electrode terminal 48A is connected to the lead wire 16B via the through hole 26C.

Subsequently, a partially stabilized zirconium powder containing 5.2 mol % of $Y_2O_3$, an organic solvent, and a dispersant are subjected to dispersion mixing in a trommel, and predetermined amounts of a binder and a viscosity adjuster are added to the mixture, followed by wet mixing, thereby preparing a slurry. A sheet is molded from the slurry by a doctor blade method, followed by annealing, thereby obtaining a green sheet that is to be used as the solid electrolyte layer 4C.

The reference electrode 6C and the lead wires 40 and 42 are formed on a left end of an upper surface of the solid electrolyte layer 4C by screen printing. An electrode paste containing Pt, $Y_2O_3$ (shared green body), a binder, and an organic solvent may be used for the lead wires 40 and 42 and the reference electrode 6C.

Subsequently, the insulation layer 29 is formed in such a fashion as to cover the lead wires 40 and 42 by screen printing. The printing is performed so as not to cover the reference electrode 6C and a leading end of the lead wire connected to the reference electrode 6C. Also, rear end of the lead wires 40 and 42 are not covered with the insulation layer 29 and are exposed as the electrode terminals 40A and 42A.

Meanwhile, the insulation layer 28 is formed on a lower surface of the solid electrolyte layer 4C by screen printing.

The insulation layer 26 and the solid electrolyte layer 4C are laminated in such a fashion that the insulation layer 28 on the lower surface of the solid electrolyte layer 4C is opposed to the insulation layer 26, and a desired sensor element shape is obtained by cutting. This laminate is subjected to degreasing at 400° C., followed by calcination at 1500° C.

Subsequently, the detection electrode 2C is printed and dried on an upper surface of the solid electrolyte layer 4C in such a fashion as to partially overlap with the leading end of the lead wire 42, followed by calcination at 1000° C.

Further, the selective reaction layer 8C is formed on a surface of the detection electrode 2C by screen printing, followed by drying and calcination at 750° C. Subsequently, the protection layer 9C is formed on a surface of the selective reaction layer 8C by screen printing and drying, and the whole body is calcinated at 750° C., thereby obtaining the sensor element 10C.

The selective reaction layer 8C, the protection layer 9C, and the second protection layer 11 may have compositions that are the same as those of the first exemplary embodiment. Also, it is possible to use the reaction electrode 2B used in the second exemplary embodiment without forming the detection electrode 2C and the selective reaction layer 8C.

This invention is not limited to the foregoing exemplary embodiments. This invention is applicable to various ammonium gas sensors that detect an ammonium concentration from an electromotive force occurred between a detection electrode and a reference electrode via a solid electrolyte layer. The cylindrical ammonium gas sensor is exemplified in the foregoing exemplary embodiment, but this invention is applicable to the plate-like ammonium gas sensor disclosed in U.S. Patent Application Publication No. 2007/0045114. For example, the second protection layer may be provided on the reference electrode 6 in the first exemplary embodiment. In this case, the second protection layer may have a composition same as or different from that of the protection layer 9A. Also, the protection layer 9C and the second protection layer 11 are separated from each other in the third exemplary embodiment, but the protection layers may be formed integrally. Also, the detection electrode and the reference electrode are aligned on one surface of the solid electrolyte layer in the third exemplary embodiment, but the detection electrode and the reference electrode may be opposed to opposite surfaces of the solid electrolyte layer.

It is needless to mention that this invention is not limited to the foregoing exemplary embodiments but encompasses various modifications and equivalents within the spirit and scope of this invention.

Hereinafter, this invention will specifically be described in conjunction with examples, but this invention is not of course limited to the examples.

Example 1

An electromotive force type ammonium gas sensor according to the first exemplary embodiment was produced.

A powder of a material (partially stabilized zirconium containing 4.5 mol % of $Y_2O_3$, for example) for a solid electrolyte layer is filled, and the powder was pressure-molded into a bottomed cylinder, followed by calcination (at about 1490° C., for example), thereby obtaining the solid electrolyte layer 4. Subsequently, non-electrolytic Pt plating was performed on an inner surface of the solid electrolyte layer 4 to form a Pt layer to be used as a reference electrode 6. After dispersion-mixing an Au powder, a zirconium powder, an organic solvent, and a dispersant, predetermined amounts of a binder and a viscosity adjuster were added, and wet mixing was performed for 4 hours to obtain an Au-based paste. In the Au-based paste, 10 wt % of the zirconium powder was contained with respect to 100 wt % of the Au powder. This Au-based paste was printed and dried on a part to be used as a detection electrode 2A and a lead wire on an outer surface of the solid electrolyte layer 4, and the whole body was calcinated (at 1000° C. for 1 hour) to form the detection electrode 2A and the lead wire.

After performing dispersion mixing of a vanadium oxide ($V_2O_5$) powder and a bismuth oxide ($Bi_2O_3$) powder prepared in a molar ratio of 1:1, an organic solvent, and a dispersant in a mortar for 4 hours using a stone mill, predetermined amounts of a binder and a viscosity adjuster were added, and a wet mixing was performed for 4 hours to prepare a $BiVO_4$-paste. This $BiVO_4$-spinel mixture paste was printed and dried in such a fashion as to cover the detection electrode 2A to obtain a selective reaction layer precursor.

Subsequently, after performing dispersion mixing of a vanadium oxide ($V_2O_5$) powder and a bismuth oxide ($Bi_2O_3$ powder prepared in a molar ratio of 1:1, a spinel ($MgAl_2O_4$) powder, an organic solvent, and a dispersant in a mortar for 4 hours using a stone mill, predetermined amounts of a binder and a viscosity adjuster were added, and a wet mixing was performed for 4 hours to prepare a $BiVO_4$-spinel mixture paste. This $BiVO_4$-spinel mixture paste was printed and dried in such a fashion as to cover the selective reaction layer precursor to obtain a protection layer precursor. In the $BiVO_4$-spinel mixture paste, a sum of the $V_2O_5$ powder and the $Bi_2O_3$ powder was 5 mol % with respect to 95 mol % of the spinel powder.

The whole body was calcinated at 750° C. for 10 minutes to obtain a selective reaction layer 8 and a protection layer 9A, thereby obtaining a sensor element 10A. In this case, a thickness of the selective reaction layer 8 was 20 μm, and a thickness of the protection layer 9A was 30 μm. The thus-obtained sensor element 10A was assembled as the ammonium gas sensor 100 as described above.

Example 2

An electromotive force type ammonium gas sensor according to the second exemplary embodiment was produced.

That is, a sensor element 10B was produced in the same manner as in Example 1 except for not using the Au-based paste of Example 1, using the $BiVO_4$-based paste for forming a reaction electrode 2B and lead wires, and forming a protection layer 9B by using the $BiVO_4$-spinel mixture paste in such a fashion that the protection layer 9B covers the reaction electrode 2B, and the sensor element 10B was assembled as the ammonium gas sensor.

After paste printing a detection electrode precursor and a protection layer precursor, the whole body was calcinated at 750° C. for 10 minutes to form the reaction electrode 2B and the protection layer 9B. In this case, a thickness of the reaction electrode 2B was 20 μm, and a thickness of the protection layer 9B was 30 μm.

Example 3

A sensor element 10A was produced in the same manner as in Example 1 except for changing the sum (=$BiVO_4$) of the $V_2O_5$ powder and the $Bi_2O_3$ powder in the $BiVO_4$-spinel mixture paste to 1 mol % with respect to 99 mol % of the spinel powder when forming a protection layer 9A, and the sensor element 10A was assembled as an ammonium gas sensor.

Example 4

A sensor element 10A was produced in the same manner as in Example 1 except for changing the sum (=$BiVO_4$) of the $V_2O_5$ powder and the $Bi_2O_3$ powder in the $BiVO_4$-spinel mixture paste to 10 mol % with respect to 90 mol % of the spinel powder when forming a protection layer 9A, and the sensor element 10A was assembled as an ammonium gas sensor.

Example 5

A sensor element 10A was produced in the same manner as in Example 1 except for changing the sum (=$BiVO_4$) of the $V_2O_5$ powder and the $Bi_2O_3$ powder in the $BiVO_4$-spinel mixture paste to 12 mol % with respect to 88 mol % of the spinel powder when forming a protection layer 9A, and the sensor element 10A was assembled as an ammonium gas sensor.

Example 6

A sensor element 10A was produced in the same manner as in Example 1 except for changing the sum (=$BiVO_4$) of the $V_2O_5$ powder and the $Bi_2O_3$ powder in the $BiVO_4$-spinel mixture paste to 15 mol % with respect to 85 mol % of the spinel powder when forming a protection layer 9A, and the sensor element 10A was assembled as an ammonium gas sensor.

Example 7

A sensor element 10A was produced in the same manner as in Example 1 except for changing the sum (=$BiVO_4$) of the $V_2O_5$ powder and the $Bi_2O_3$ powder in the $BiVO_4$-spinel mixture paste to 20 mol % with respect to 80 mol % of the spinel powder when forming a protection layer 9A, and the sensor element 10A was assembled as an ammonium gas sensor.

Example 8

A sensor element 10A was produced in the same manner as in Example 1 except for printing a selective reaction layer precursor using the above-described $BiVO_4$-spinel mixture paste after printing the Au-based paste on a part to be used as the detection electrode and the lead wires without calcinating the Au-based paste, forming the protection layer precursor by printing a paste obtained by not blending the $V_2O_5$ powder and the $Bi_2O_3$ powder in the $BiVO_4$-spinel mixture paste (i.e. a pate containing only the spinel powder was used), and calcinating the whole body at 1000° C. for 10 minutes, and the sensor element 10A was assembled as an ammonium gas sensor.

Comparative Example

A sensor element 10B was produced in the same manner as in Example 2 except for not blending the $V_2O_5$ powder and the $Bi_2O_3$ powder in the $BiVO_4$-spinel mixture paste (i.e. a pate containing only the spinel powder was used), and the sensor element 10B was assembled as an ammonium gas sensor.

Evaluation

1. Contact of Protection Layer

An adhesive tape [mending tape; T-112; manufactured by Kokuyo Co., Ltd. (12 mm×35 mm)] was strongly pressed against each of the protection layers on the outer surfaces of the sensor elements before assembly to an ammonium gas sensor and then peeled off to visually judge absence/presence of stripping-off of the protection layer. The stripping test method was performed with reference to "Method for Testing Contact of Plating" of JISH8504. The sensor element of which the protection layer adhered to the tape was evaluated to be x as the protection layer that is subject to stripping-off, and the sensor element of which the protection layer did not adhere to the tape was evaluated to be o as the protection layer that is free from the stripping-off.

2. $BiVO_4$ Concentration in Protection Layer in the Vicinity of Interface between Protection Layer and Underlying Layer After obtaining a sectional structure of the protection layer by cutting each of the sensor elements before assembly to an ammonium gas sensor along the longitudinal direction, a region of 1 $\mu m^2$ (1 μm×1 μm) from the interface between the protection layer and the underlying layer to the protection layer was measured by EPMA (X-ray Micro-Analyzer). A concentration of $BiVO_4$ contained in the region was obtained by conversion of B and V detected by EPMA.

3. Sensor Characteristics (Sensitivity) Evaluation 3-1. Sensor Initial Sensitivity The ammonium gas sensors of Examples and Comparative Example were mounted in a gas stream of a model gas generation apparatus to evaluate initial sensitivity of each of the sensors. A gas temperature of the model gas was set to 280°

C.; an element control temperature (heating with heater) was set to 650° C.; and a composition of a reference gas was set to $O_2$=10%, $CO_2$=5%, $H_2O$=5%, $N_2$=balance, and $NH_3$=0 ppm. Also, a composition of a measured gas was set to $O_2$=10%, $CO_2$=5%, $H_2O$=5%, $N_2$=balance, and $NH_3$=100 ppm. A potential difference between the detection electrode and the reference electrode when supplying the gas from the model gas generation apparatus was measured to detect the sensor initial sensitivity. The sensor sensitivity was defined by an electromotive force in measurement of the measured gas—basic electromotive force (electrometric force when not exposed to the measured gas (i.e. electrometric force in measurement of the reference gas)).

3-2. Demonstration Test

Each of the ammonium gas sensors of Examples and Comparative Example was attached to an engine for demonstration to evaluate sensor characteristics by actually operating the engine. A diesel engine having an emission of 3.0 L was used as the engine, and the ammonium gas sensor was attached to a DOC (Diesel Oxidation Catalyst) muffler and a rear stream of a DPF (Diesel Particulate Filter) of the engine.

A cycle of idling the engine for 10 minutes and operating the engine for 30 minutes at 3000 rpm was repeated for 500 hours as a demonstration test.

After the demonstration test, the sensor was detached from the demonstration engine and placed in a gas stream of the above-explained model gas generation apparatus, and a potential difference between the detection electrode and the reference electrode was measured to detect sensor sensitivity after the demonstration test. The sensor sensitivity was defined by an electromotive force in measurement of the measured gas—basic electromotive force (electromotive force when not exposed to the measured gas (i.e. electrometric force in measurement of the reference gas)).

Figure 7:
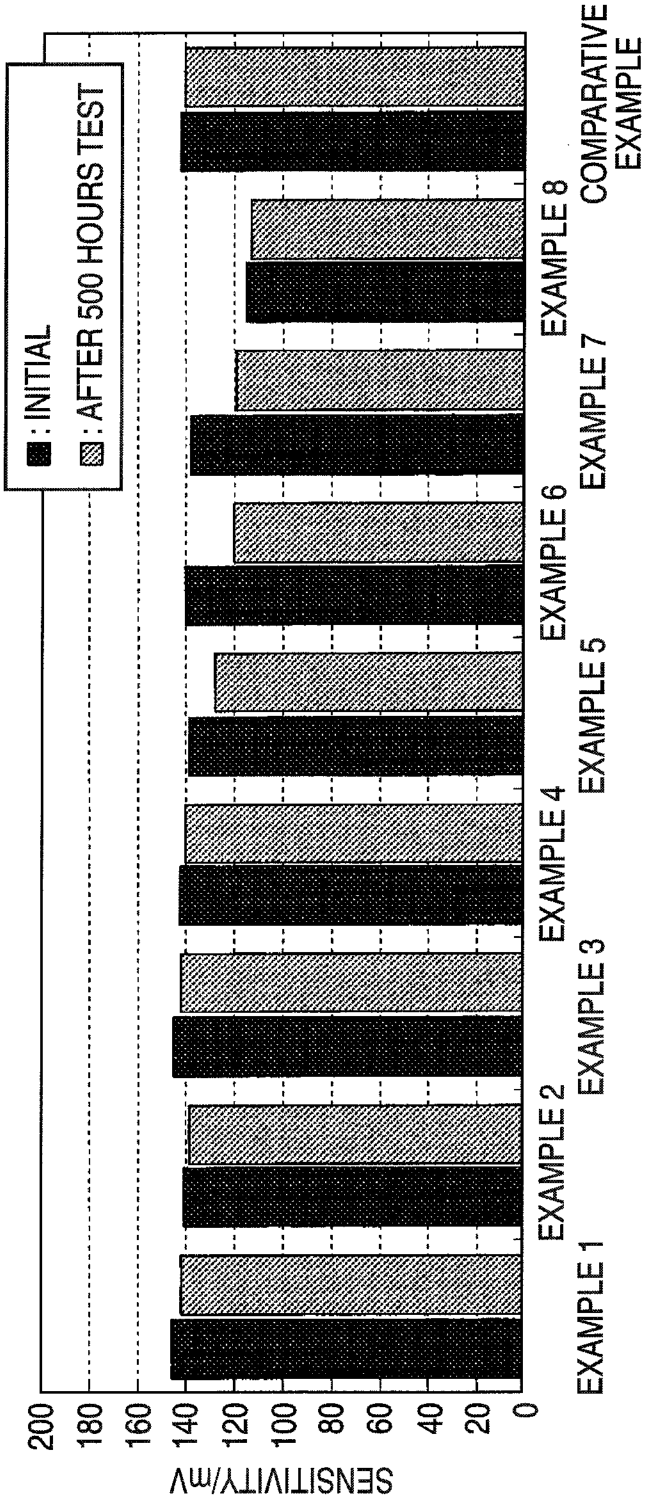
FIG. 7 is a diagram showing sensor sensitivity after 500 hours test.

The obtained results are shown in Table 1 and FIG. 7.

from the underlying layer (selective reaction layer) to the protection layer ($BiVO_4$ concentration in the protection layer in the vicinity of the interface between the protection layer and the underlying layer is 0.1 mol %) as a result of the calcination at high temperature (1000° C.). Note that the slight deterioration in sensitivity of Example 8 is considered to be attributable to the calcination at 1000° C. that caused a particle growth of $BiVO_4$, a reduction in gas diffusion speed, and burning of a part of ammonium.

In contrast, in Comparative Example where the protection layer does not contain the component ($BiVO_4$) of the underlying layer (reaction electrode), contact of the protection layer is inferior. It is revealed that $BiVO_4$ is not diffused by the calcination at the ordinary calcination temperature (750° C.).

As to the sensor sensitivity evaluation, the sensor sensitivity of Examples 5 to 7 is deteriorated after the demonstration test (for 500 hours) as compared to the rest of Examples. It is considered that such sensor sensitivity deterioration occurred since ammonium was prevented from permeating to the underlying layer due to the porous material that was clogged up with a certain reaction product generated between $BiVO_4$ and a component (oil component, P, Si, or the like) in the exhaust gas. From such result, it is proved that the $BiVO_4$ concentration in the protection layer in the vicinity of the interface between the protection layer and the underlying layer may preferably be 10 mol % or less.

In Example 8, the content of $BiVO_4$ in a thickness direction of the protection layer 9A is shown in Tale 2. Measurement of the $BiVO_4$ content was conducted by identifying a crystal structure of oxide obtained from a sectional structure of the protection layer 9A and containing the component A or the

TABLE 1

| | | Ex. 1 | Ex. 2 | Ex. 3 | Ex. 4 | Ex. 5 | Ex. 6 | Ex. 7 | Ex. 8 | Comp. Ex. |
|---|---|---|---|---|---|---|---|---|---|---|
| Selective reaction layer | | Provided | Not Provided | Provided | Provided | Provided | Provided | Provided | Provided | Not Provided |
| $BiVO_4$ in Protection Layer before Calcination | | Provided | Provided | Provided | Provided | Provided | Provided | Provided | Not Provided | Not Provided |
| Calcination Temperature (° C.) of Protection Layer and Underlying Layer | | 750 | 750 | 750 | 750 | 750 | 750 | 750 | 1000 | 750 |
| $BiVO_4$ Concentration in the Vicinity of Interface between Protection Layer and Underlying Layer (mol %) | | 5.1 | 5.0 | 1.1 | 9.8 | 12.1 | 15.0 | 19.7 | 0.1 | 0 |
| Contact of Protection Layer | | ○ | ○ | ○ | ○ | ○ | ○ | ○ | ○ | x |
| Sensor Sensitivity (mV) | Initial | 146 | 141 | 145 | 143 | 139 | 140 | 138 | 115 | 142 |
| | After 500 Hours Test | 142 | 139 | 142 | 140 | 128 | 120 | 119 | 113 | 140 |
| | Change Amount | 4 | 2 | 3 | 3 | 11 | 20 | 19 | 2 | 2 |

As is apparent from Table 1, in the case of Examples in which the component ($BiVO_4$) of the underlying layer (the reaction electrode in Example 2, and the selective reaction layer in the rest of Examples) is contained in the protection layer, the contact of the protection layer is excellent. In Example 8, though $BiVO_4$ is not contained in the protection layer before calcination, it is revealed that $BiVO_4$ diffused component M by employing XRD (X-ray diffraction) and XPS (X-ray photoelectron Spectroscopic Analysis). The $BiVO_4$ content in the interface between the protection layer 9A and the selective reaction layer 8 was obtained by detecting a concentration of $A_xM_yO_z$ (calculated by conversion from the component A and the component M) contained in a region of 1 $\mu m^2$ (1 $\mu m \times 1$ $\mu m$) from the interface between the protection layer 9A and the selective reaction layer 8 to the protection layer 9A by EPMA (X-ray micro-analyzer).

The obtained results are shown in Table 2.

TABLE 2

| Distance from Interface between Protection Layer and Selective Reaction Layer to Inside of Protection Layer (μm) | In the Vicinity of Interface | 5 | 10 | 20 | Protection Layer Surface |
|---|---|---|---|---|---|
| $BiVO_4$ Concentration (mol %) | 0.10 | 0.04 | 0.01 | 0.00 | 0.00 |

As is apparent from Table 2, the $BiVO_4$ concentration is lowered along with an increase in distance from the interface between the selective reaction layer 8 and the protection layer 9A (concentration inclination), and is not contained in the vicinity of the surface of the protection layer 9A that is distant from the interface by 20 μm or more. From the above results, it is proved that the oxide content in the protection layer 9A may preferably be such that the oxide content in the vicinity of the surface is smaller than the oxide content in the vicinity of the interface of the selective reaction layer 8. Also, it is proved that a thickness of a part of the protection layer 9A where the oxide content is 0.1 to 10 mol % may preferably be equal to or less than a thickness of the selective reaction layer 8.

As described above, there is provided an ammonium gas sensor of one of the exemplary embodiments comprises: a solid electrolyte layer having oxygen ion conductivity; a detection electrode formed on one surface of the solid electrolyte layer; a reference electrode that is a counter electrode of the detection electrode; a selective reaction layer covering the detection electrode; and a protection layer covering the selective reaction layer and made from a porous material; wherein the detection electrode comprises a noble metal as a main component; the selective reaction layer comprises oxide represented by $A_xM_yO_z$ (A is one or more kinds of metal; M is vanadium, tungsten, or molybdenum; and x, y, z are atomic ratios) as a main component; and the protection layer comprises the oxide that is in an amount smaller than a content of the oxide comprised in the selective reaction layer.

With such constitution, since the oxide $A_xM_yO_z$ that is the main component of the underlying layer (selective reaction layer) is contained in the protection layer, a contact between the protection layer and the selective reaction layer is improved. Further, since the content of the oxide $A_xM_yO_z$ contained in the protection layer is made smaller than that of the selective reaction layer, the protection layer is less subject to clogging, and burning of ammonium due to a generated reaction product is suppressed, thereby suppressing deterioration of sensitivity of the sensor.

Also, the ammonium gas sensor of one of the exemplary embodiments comprises: a solid electrolyte layer having oxygen ion conductivity; a reaction electrode formed on one surface of the solid electrolyte layer; a reference electrode that is a counter electrode of the detection electrode; and a protection layer covering the reaction electrode and made from a porous material; wherein the reaction electrode comprises oxide represented by $A_xM_yO_z$ (A is one or more kinds of metal; M is vanadium, tungsten, or molybdenum; and x, y, z are atomic ratios) as a main component; and the protection layer comprises the oxide that is in an amount smaller than a content of the oxide comprised in the reaction electrode.

With such constitution, since the oxide $A_xM_yO_z$ that is the main component of the underlying layer (reaction electrode) is contained in the protection layer, a contact between the protection layer and the reaction electrode is improved. Further, since the content of the oxide $A_xM_yO_z$ contained in the protection layer is smaller than that of the reaction electrode, the protection layer is less subject to clogging, and burning of ammonium due to a generated reaction product is suppressed, thereby suppressing deterioration of sensitivity of the sensor.

In $A_xM_yO_z$ representing the oxide, A may preferably be one or more kinds selected from the group consisting of bismuth, lanthanum, strontium, calcium, copper, gadolinium, neodymium, yttrium, samarium, and magnesium.

With such constitution, it is possible to improve the ammonium gas electivity with the contact between the protection layer and the underlying layer being maintained.

The oxide may preferably be represented by $BiVO_4$.

With such constitution, it is possible to further improve the ammonium gas selectivity with the contact between the protection layer and the underlying layer being maintained.

The oxide content in the protection layer in the vicinity of an interface between the protection layer and the selective reaction layer or the reaction electrode may preferably be 10 mol % or less.

With such constitution, it is possible to sufficiently maintain the contact between the reaction electrode or the selective reaction layer and the protection layer as well as to prevent the sensitivity of the sensor from being deteriorated by use due to the reason such as a certain reaction product generated between the oxide $A_xM_yO_z$ and a component in a gas to be measured. The sensor sensitivity can be deteriorated in some cases when the oxide content in the protection layer exceeds 10 mol %.

The oxide content in the protection layer may preferably be smaller in the vicinity of a surface of the protection layer as compared to that in the vicinity of a boundary between the protection layer and the selective reaction layer or the reaction electrode.

With such constitution, it is possible to sufficiently maintain the contact between the reaction electrode or the selective reaction layer and the protection layer as well as to further prevent the sensitivity of the sensor from being deteriorated by use due to the reason such as a certain reaction product generated between the oxide $A_xM_yO_z$ and a component in a gas to be measured.

The oxide content in the protection layer in the vicinity of the interface between the protection layer and the selective reaction layer or the reaction electrode may preferably be 0.1 mol % or more.

With such constitution, it is possible to further improve the contact between the protection layer and the selective reaction layer or the reaction electrode by positively adding the oxide to the protection layer. The wording “positively adding” means to add the oxide to a material forming the protection layer or to dissipate the oxide in the protection layer from the selective reaction layer or the reaction electrode.

A thickness of a part of the protection layer that enables the oxide content of 0.1 to 10 mol % may preferably be equal to or less than a thickness of the selective reaction layer or the reaction electrode.

With such constitution, it is possible to sufficiently maintain the contact between the selective reaction layer and the protection layer as well as to further prevent the sensitivity of the sensor from being deteriorated by use due to the reason such as a certain reaction product generated between the oxide $A_xM_yO_z$ and a component in a gas to be measured.

The ammonium gas sensor comprises a second protection layer covering the reference electrode, and the second protection layer does not contain the oxide contained in the selective reaction layer or the reaction electrode.

With such constitution, it is possible to prevent the sensor sensitivity from being deteriorated as well as to protect the reference electrode.

The selective reaction layer or the reaction electrode may preferably comprise at least one of $A_xO_z$ and $M_yO_z$ (A is one or more kinds of metal; M is vanadium, tungsten, or molybdenum; and x, y, and z are atomic ratios).

With such constitution, it is possible to further improve the ammonium selectivity.

What is claimed is:

1. An ammonium gas sensor comprising:

a solid electrolyte layer having oxygen ion conductivity;

a detection electrode formed on one surface of the solid electrolyte layer;

a reference electrode that is a counter electrode of the detection electrode;

a selective reaction layer covering the detection electrode; and a protection layer covering the selective reaction layer and made from a porous material;

wherein the detection electrode includes a noble metal as a main component;

the selective reaction layer includes an oxide represented by $A_xM_yO_z$ as a main component, where A is one or more kind(s) of metal, M is vanadium, tungsten, or molybdenum and x, y, z are atomic ratios;

the protection layer includes the oxide of the selective reaction layer in an amount smaller than a content of the oxide included in the selective reaction layer, and contains at least one selected from the group consisting of $MgAl_2O_4$, $SiO_2$, $SiO_2/Al_2O_3$, zeolite and SiC as a main component; and the detection electrode is exposed to the gas to be measured.

2. The ammonium gas sensor according to claim 1, wherein in $A_xM_yO_z$ representing the oxide, A is one or more kind(s) selected from the group consisting of bismuth, lanthanum, strontium, calcium, copper, gadolinium, neodymium, yttrium, samarium, and magnesium.

3. The ammonium gas sensor according to claim 1, wherein the oxide is represented by $BiVO_4$.

4. The ammonium gas sensor according to claim 1, wherein the oxide content in the protection layer in the vicinity of an interface between the protection layer and the selective reaction layer is 10 mol % or less.

5. The ammonium gas sensor according to claim 1, wherein the oxide content in the protection layer is smaller in the vicinity of a surface of the protection layer as compared to that in the vicinity of an interface between the protection layer and the selective reaction layer.

6. The ammonium gas sensor according to claim 1, wherein the oxide content in the protection layer in the vicinity of an interface between the protection layer and the selective reaction layer is 0.1 mol % or more.

7. The ammonium gas sensor according to claim 1, wherein a thickness of a part of the protection layer that includes the oxide content of 0.1 to 10 mol % is equal to or less than a thickness of the selective reaction layer.

8. The ammonium gas sensor according to claim 1, wherein the ammonium gas sensor comprises a second protection layer covering the reference electrode, and the second protection layer does not contain the oxide included in the selective reaction layer.

9. The ammonium gas sensor according to claim 1, wherein the selective reaction layer comprises at least one of $A_xO_z$ and $M_yO_z$, where A is one or more kind(s) of metal, M is vanadium, tungsten, or molybdenum, and x, y, and z are atomic ratios.

* * * * *